Figure 1:
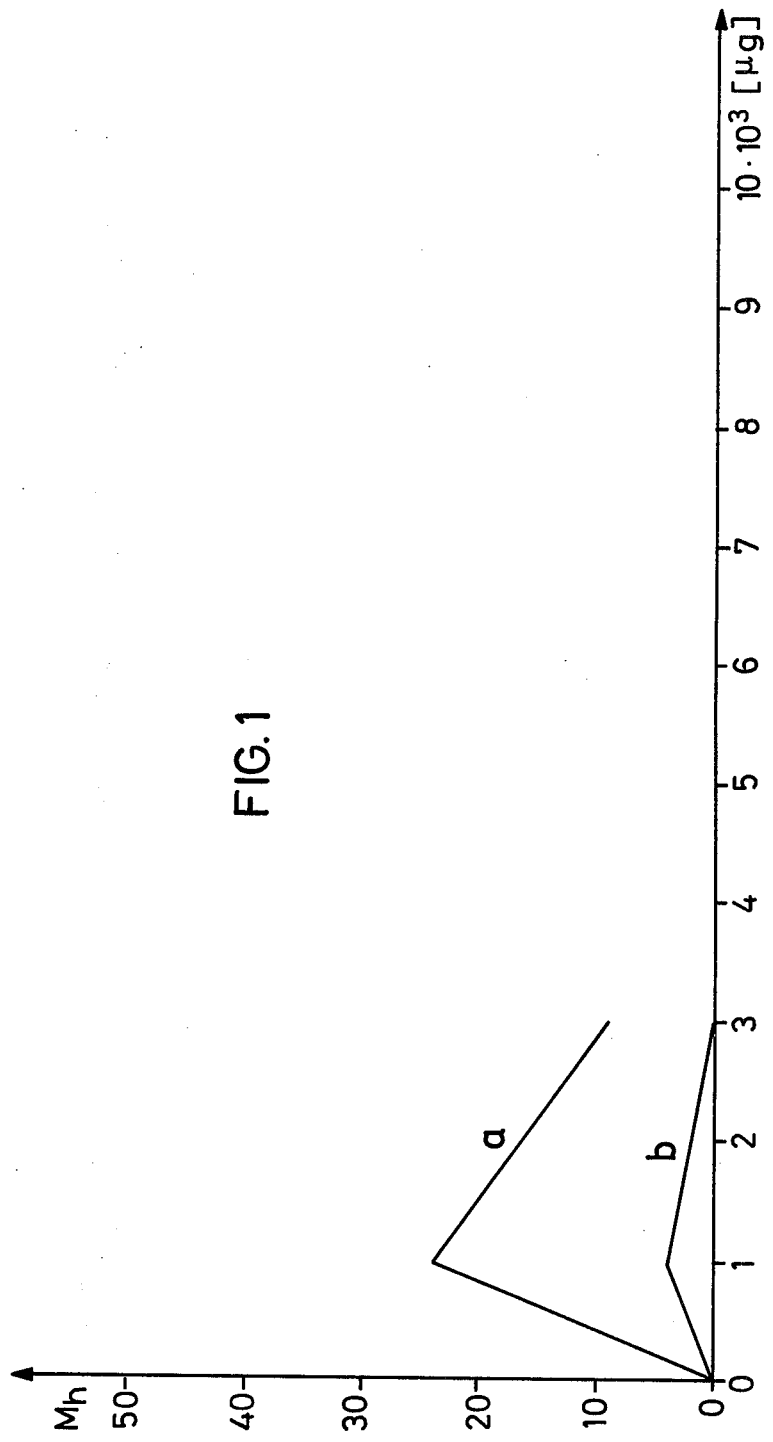

United States Patent [19]

Burg et al.

[11] 4,150,238

[45] Apr. 17, 1979

[54] ANTIVIRAL POLYMER

[75] Inventors: Karlheinz Burg, Naurod; Karl-Friedrich Mück, Wiesbaden; Arthur Neufahrt, Hattersheim am Main; Heinrich Rolly, Kelkheim, all of Fed. Rep. of Germany

[73] Assignee: Hoechst Aktiengesellschaft, Frankfurt am Main, Fed. Rep. of Germany

[21] Appl. No.: 757,503

[22] Filed: Jan. 7, 1977

Related U.S. Application Data

[63] Continuation of Ser. No. 527,706, Nov. 27, 1974, abandoned.

[30] Foreign Application Priority Data

Nov. 30, 1973 [DE] Fed. Rep. of Germany ....... 2359621

[51] Int. Cl.$^2$ ............................................. C07C 69/54

[52] U.S. Cl. ...................................... 560/205; 424/81
[58] Field of Search ..................... 560/216, 205, 16; 424/81

[56] References Cited

PUBLICATIONS

De Somer, R. et al., Jrnl. of Virology, Sep. 1968, pp. 878–885.
De Somer, Symposia Series in Immunobiological Standardization, vol. 14, 1970, pp. 221–226.
De Clercq et al., Ach. Intern. Med., vol. 126, Jul. 1970.

*Primary Examiner*—Paul J. Killos
*Attorney, Agent, or Firm*—Curtis, Morris & Safford

[57] ABSTRACT

Poly(acrylic acid) salts having specific structural characteristics, which salts are useful for combatting virus diseases.

5 Claims, 4 Drawing Figures

ANTIVIRAL POLYMER

This is a continuation, of application Ser. No. 527706, filed Nov. 27, 1974, now abandoned.

It is a known fact that copolymers by divinyl ether and maleic acid anhydride can be used for combating the virus provoking aphtous fever (cf. U.S. Pat. No. 3,624,218). It is also known that poly(vinyl-sulfonic acid) of various degrees of sulfonation and different molecular weights can be used for prophylactic steps against this virus (cf. U.S. Pat. No. 3,466,365). Moreover, it is known that poly(acrylic acid) shows anti-viral action [cf. Journal of Virology, Vol.2, No.9 (1968), pages 878 and 886, Symp. Series immunobiol. Standard., Vol. 14 (1970), page 221]. All the aforementioned polymers are obtained by free-radical polymerization and, as a result, have a broad molecular weight distribution.

The present invention relates to salts of a poly(acrylic acid) having an average molecular weight (viscosity average) of from 5,000 to 40,000, an unevenness of the molecular weight of from 1.1 to 2, an isotactic portion of at least 75 weight percent and at most 5 weight percent of unsaponified portions.

The average molecular weight the poly(acrylic acid) is preferably from 8,000 to 30,000 and especially from 10,000 to 25,000, the unevenness of the molecular weight is preferably from 1.1 to 1.5 and the isotactic portion is preferably from 90 to 98 weight percent. For determination of the average molecular weight, the polymer is dissolved in chloroform and the viscosity of the solution is determined at a polymer concentration of 0.3 g/100 ml, of 0.6 g/100 ml and of 0.9 g/100 ml at a temperature of 30° C. After having graphically determined the viscosity limit $[\eta]$ at which the concentration c=0, the molecular weight $\overline{M}$ is calculated from the equation $[\eta] = 1.4 \times 10^{-4} \times \overline{M}^{-0.72}$ [(cf. Macromolekular Syntheses, Vol. 1 (1963), page 25]. By "unevenness of the molecular weight" is to be understood the quotient of the weight average of the molecular weight and the numerical average of the molecular weight; this value is determined by means of gel permeation chromatography. The isotactic portion is determined by means of nuclear magnetic resonance spectroscopy.

The salt of poly(acrylic acid) according to the invention is prepared in such a way that an ester of acrylic acid with an alcohol branched in α-position is polymerized in the presence of an anionically active catalyst at a temperature from 0 to −80° C. in an inert organic solvent tightly separated from oxygen and water, the formed atactic polymer is eliminated to a great extent, the remaining polymer being acidolytically saponified and the poly(acrylic acid) obtained which is essentially isotactic, being neutralized.

Special use is made of esters of acrylic acid with monovalent alcohols branches in α-position having 3,4,5 or 6 carbon atoms, for example acrylic acid cyclohexyl ester, acrylic acid isopropyl ester and acrylic acid tert.-butyl esters. Alkali metal alcoholates having from 1 to 4 carbon atoms, such as sodium methylate, sodium ethylate, sodium isopropylate and sodium-tert.-butylate are suitable catalysts being anionically active; suitable are also aliphatic alkali metal alkyles such as tert.-butyl lithium and isopropyl sodium, as well as—preferably—Grignard compounds having from 1 to 7 carbon atoms such as ethyl magnesium bromide, isopropyl magnesium bromide, tert.-butyl magnesium chloride, phenyl magnesium bromide, benzyl magnesium bromide and benzyl magnesium chloride. The catalyst quantity generally amounts to from 0.01 to 0.5 preferably from 0.05 to 0.3 mole per mole of monomer.

Polymerization of the acrylic acid ester is carried out preferably at a temperature of from −60° C. to −80° C. As inert organic solvents are used those having melting points below −80° C., especially monoalkylbenzenes such as toluene, ethylbenzene and propylbenzene. The polymerization requires from 10 minutes to 24 hours, preferably from 1 to 6 hrs, depending on the quantity of monomer used.

The poly(acrylic acid ester) obtained upon polymerization can include up to 25, preferably from 10 to 2 weight percent of atactic portions. These are eliminated from the reaction mixture to a great extent, the removal being carried out, for example, by agitation with isopropanol at a temperature of from 15° to 30° C., preferably at room temperature, for a period from 12 to 24, preferably from 14 to 18 hours.

The average molecular weight of the individual poly(acrylic acid ester) can be adjusted by means of the quantity of the catalyst used, the average molecular weight being from 7,900 to 64,000, preferably from 13,000 to 40,000.

The essentially isotactic poly(acrylic acid ester) is saponified acidolytically. Convenient saponification media are especially mixtures of water and strong organic acids, the quantity of water being from 60 to 1, preferably from 40 to 15, percent by volume and the quantity of acid being from 40 to 99, preferably from 60 to 85, percent by volume. As strong organic acids mono-, di-, or tri-halogenated acetic acids are especially used, for example monochloroacetic acid, monofluoroacetic acid, trichloroacetic acid and trifluoroacetic acid. The quantity of the hydrolysis medium surpasses from 5 to 20 times, preferably from 8 to 15 times the quantity by weight of the polymer to be hydrolyzed, i.e. a solution of the polymer is used which contains from 20 to 5, preferably from about 12 to 7 weight percent of poly(acrylic acid ester). The hydrolysis is carried out—as a rule—at the boiling temperature of the hydrolysis medium, preferably at a temperature of from 80 to 120° C. The operation lasts normally from 50 to 90, preferably from 60 to 80, hours. Subsequently, the poly(acrylic acid) obtained is purified by dialysis against water and submitted to vacuum freeze drying.

In case the unevenness of the molecular weight of the poly(acrylic acid ester) obtained according to the process of the invention surpasses the value of 2, the product is submitted to precipitating fractionation. As solvents are used for this purpose the above mentioned inert aromatic solvents aliphatic hydrocarbons having from 5 to 8 carbon atoms, preferably straight-chain materials such as n-pentane, n-hexane, n-heptane and n-octane, are used as precipitating agents.

The poly(acrylic acid) is neutralized with organic and inorganic bases, especially with basic salts and preferably with alkali metal salts of polybasic mineral acids. For example, suitable bases are sodium hydroxide, potassium hydroxide, ammonia, primary and secondary aliphatic or aromatic amines with hydrocarbon radicals having each from 1 to 6, preferably 1, 2 or 3 carbon atoms, e.g. methylamine, ethylamine, propylamine, aniline, dimethylamine, diethylamine and dipropylamine, furthermore sodium dihydrogen phosphate, disodium hydrogen phosphate, ammonium dihydrogen phosphate, sodium carbonate and sodium hydrogen carbonate.

The salt according to the invention, preferably an alkali metal salt, of poly(acrylic acid) is a suitable medicine especially for prophylactic treatment to combat viral infections and also for therapeutic treatment immediately following the viral infection.

The antiviral efficiency of salts of isotactic poly(acrylic acids) having a high degree of isotacticity and a narrow range of molecular weight distribution surpasses—at identical average molecular weight—that of isotactic poly(acrylic acids) hving a broader range of molecular weight distribution. Moreover, it is much higher than that of known atactic poly(acrylic acids) of identical molecular weight, regardless of whether the atactic polyacids have a narrow or a broad range of molecular weight distribution.

The isotactic poly(acrylic acid) salt shows—in vivo—better antiviral properties than atactic material. In vitro either a direct physical bonding to the virus and a pH-dependent inactivation of the virus is occurring, or, due to an electrostatic modification of the cell surface, the penetration of the virus into the cell and thus the infection itself is being impeded. The isotactic poly(acrylic acid) salt—in vivo—reduces the consequences of the infection after its break-out—either by inhibition of the proliferation of the virus or by increased resistance of the organism due to stimulation of the reticuloendothelial system (RES) including interferon induction and emphasized phagocytosis. It excels by a good longtime efficiency for from 8 to 10 weeks after one single administration. The interferon induction is especially well discernable at high doses.

The salt of poly(acrylic acid) according to the invention is usually administered as a solution or suspension. As solvents or suspending agents medicinically unobjectionable inert liquids, e.g. water and aqueous buffer solutions, glycols such as propylene glycol, alcohols such as glycerine, esters such as diethyl carbonate as well as oils such as peanut oil and sesame oil, are used. The pH value of the solution or the suspension is from 5 to 7.5—preferably from 6 to 7. The solution or suspension is administered either intravenously (iv), intraperitoneally (ip), intramuscularly (im), subcutaneously (sc) and—in some cases—also per os. The doses vary—generally—from 5 to 1,500 mg/kg, preferably from 50 to 500 mg/kg; for intravenous administration a dose of from 80 to 150 mg/kg is especially recommended, for intraperitoneal application a dose of from 50 to 150 mg/kg, for intramuscular administration a rate from 150 to 500 mg/kg, and for subcutaneous application a rate of also 150 to 500 mg/kg. The solution of suspension has a volume of from 0.05 to 1.0—preferably from 0.1 to 0.5 ml. In addition to the antivirally efficient substance, there may be included further additives of other therapeutic agents, e.g. antibiotics, analgetics and hypnotics.

The efficiency of the salt of poly(acrylic acid) according to the invention covers a wide range of viruses. Positive reactions are observed as well for RNA virus such as Columbia SK virus, Encephalomyocarditis virus (EMC - Theiler), influenza A virus/PR8 and vesicularstomatitis virus/strain Indiana, as well as DNA viri, e.g. Vaccinia viruses/P 71. The action against Columbia SK virus or EMC virus is tested on NMRI mice from SPF breeding stock having a weight of from 16 to 20 g, the test consisting of administering to the mice from 10 to 20 lethal doses/50% ($LD_{50}$ according to Reed and Muench) of a cerebral suspension of the virus strain to be examined. By cerebral suspension has to be understood the suspension in a buffered sodium chloride solution of the brains of mice which had been infected with the virus in question and had fallen ill. Untreated mice were killed by the infection about 7 to 9 days after administration of the cerebral suspension, death being caused by mounting paralyzation and break-down of respiration. The death by infection can be prevented with a great degree of certainty if the test mice are treated with the salt of poly(acrylic acid) according to the invention for a period of from several weeks prior to until 16 hours after the infection.

The following examples illustrate the invention:

EXAMPLE 1:

Salts of poly(acrylic acid) having diverse molecular weights are prepared as follows: Diverse quantities of a 2.3n-phenylmagnesium bromide solution in diethyl ether are injected in each case into 500 ml of absolute toluene which had been freed from oxygen by introducing nitrogen. The mixture is cooled to $-78°$ C. by means of a cooling bath and after injection of 43 ml (0.34 mole) of acrylic acid isopropyl ester stored at this temperature for 24 hours. By adding the mixture obtained into a tenfold quantity by volume of a mixture of methanol, water and hydrochloric acid (proportion by volume 20:4:1), the polymer formed precipitates (yield rates see Table 1). Subsequently the polymer is stirred for 12 hours in a tenfold quantity by volume of isopropanol at room temperature. The average molecular weight of the poly(acrylic acid ester) is determined by dissolving 0.3 g, 0.6 g or 0.9 g of the polymer in 100 ml each of chloroform and by measuring the viscosity of the solution at a temperature of 30° C. The boundary viscosity [$\eta$] at the concentration of $c=0$ is determined graphically and the molecular weight $\overline{M}$ is determined by calculation (results see Table 1). The unevenness of the molecular weight of the polymer is determined by means of gel permeation chromatography. If this value exceeds 2, an additional precipitating fractionation with benzene as solvent and n-hexane as precipitating agent is carried out subsequently.

For saponification 5 g each of the essentially isotactic For hydrolysis, the essentially isotactic poly(acrylic acid isopropyl ester) is dissolved in an 80:20 (by volume) mixture of trifluoracetic acid and water at a rate of 5 g of polymer per 100 ml of mixture and the hours. The poly(acrylic acid) precipitating from the reaction mixture is separated from the mixture by filtration. It is dissolved in hot water, submitted to dialysis against water and to vacuum freeze drying. The result obtained are 3.1 g (98.5% of the theoretical yield) of isotactic poly(acrylic acid) having a saponification ratio of 95%.

For therapeutic or prophylactic application as a salt a quantity of from 0.3 to 30.0 mg of poly(acrylic acid) pro ml is dissolved in each case in an aqueous buffer solution containing in 100 ml an amount of 5.368 g of sodium dihydrogen phosphate and of 8.746 g of disodium hydrogen phosphate and having a pH value of 7.0.

Table 1:

| Test | initiator solution (ml) | molecular weight | unevenness of molecular weight | isotactic portion (weight %) | yield (weight %) |
|---|---|---|---|---|---|
| a. | 5 | 75 000 | 1.9 | >95 | 60 |
| b. | 10 | 30 000 | 1.3 | >95 | 65 |
| c. | 13 | 20 000 | 1.2 | >95 | 70 |
| d. | 20 | 14 000 | 1.3 | >95 | 70 |
| e. | 30 | 8 000 | 1.4 | >95 | 50 |

Table 1:-continued

| Test | initiator solution (ml) | molecular weight | unevenness of molecular weight | isotactic portion (weight %) | yield (weight %) |
|---|---|---|---|---|---|
| f. | 40 | 7 000 | 1.4 | >95 | 55 |

EXAMPLE 2:

The following tests prove that the efficacy of the poly(acrylic acid) salt depends on the dose applied: Solutions according to Example 1 containing from 0.3 to 10 mg/ml of an essentially isotactic poly(acrylic acid) having an average molecular weight of 16,000, an unevenness of the molecular weight of 1.2, an isotactic portion of 95 weight percent and an unsaponified portion of less than 5 weight percent in 100 ml of the aqueous buffer solution are used. Constant quantities of these solutions with diverse concentration rates are administered by subcutaneous injection to 4 groups of 10 mice each. 24 hours after the injection the mice—as well as another group of 10 untreated specimens—(compare test a)—are infected with Columbia SK virus. The efficacy of the salt of poly(acrylic acid) results from the survival ratio shown in Table 2.

Table 2:

| Test | Dose (mg/mouse) | survival ratio (%) |
|---|---|---|
| a. | — | 0 |
| b. | 0.3 | 0 |
| c. | 1.0 | 20 |
| d. | 3.0 | 70 |
| e. | 10.0 | 80 |

EXAMPLE 3:

The following tests reveal that the efficacy of the salt of poly(acrylic acid) depends on the unevenness of the molecular weight. Use is made of the saline solution identical to that used for example 2. Diverse quantities of this solution are administered to 3 groups of 10 mice each by subcutaneous injection. In the same manner 3 further groups of 10 mice each are treated, the latter being treated with a corresponding saline solution in which the molecular weight (MW) of the poly(acrylic acid) is, however, 17,000 and the unevenness of the molecular weight (UMW) is 10. 24 hours after the injection the specimens are infected with 10 $LD_{50}$ Columbia SK virus - as well as another group of 10 untreated mice (see test a). The survival ratio (see Table 3) shows the efficacy of the salt of poly(acrylic acid).

Table 3:

| Test | Poly(acrylic) acid) | dose (mg/mouse) | survival ratio % |
|---|---|---|---|
| a | — | — | 0 |
| b | MW 16 000, UMW 1,2 | 0.3 | 0 |
| c | | 1.0 | 20 |
| d | | 3.0 | 70 |
| e | MW 17 000, UMW 10 | 0.3 | 0 |
| f | | 1.0 | 10 |
| g | | 3.0 | 40 |

EXAMPLE 4:

The following tests reveal that the efficacy of the salt of poly(acrylic acid) depends on the molecular weight of poly(acrylic acid) and on the tacticity:

A saline solution is used identical to that of Example 2, the average molecular weight values and the isotactic portions of the poly(acrylic acid) varying however; The unevenness of the molecular weight is from 1.2 to 1.4 and the unsaponified portion is a maximum of 5 weight percent. Various quantities of the saline solution are administered to groups of 10 mice each by subcutaneous injection, and 24 hours after the injection the specimens are infected with 10 $LD_{50}$ of Columbia SK virus. 14 days later the harmonic average values of the survival period of the corresponding groups are compared. The harmonic average $M_h$ of n observed values $x_1, x_2, \ldots, x_n$ is the quotient of the number n of observations and the sum of the reciprocal individual values $$M_h = \frac{n}{\frac{1}{x_1} + \frac{1}{x_2} + \ldots + \frac{1}{x_n}}$$

Figure 2:
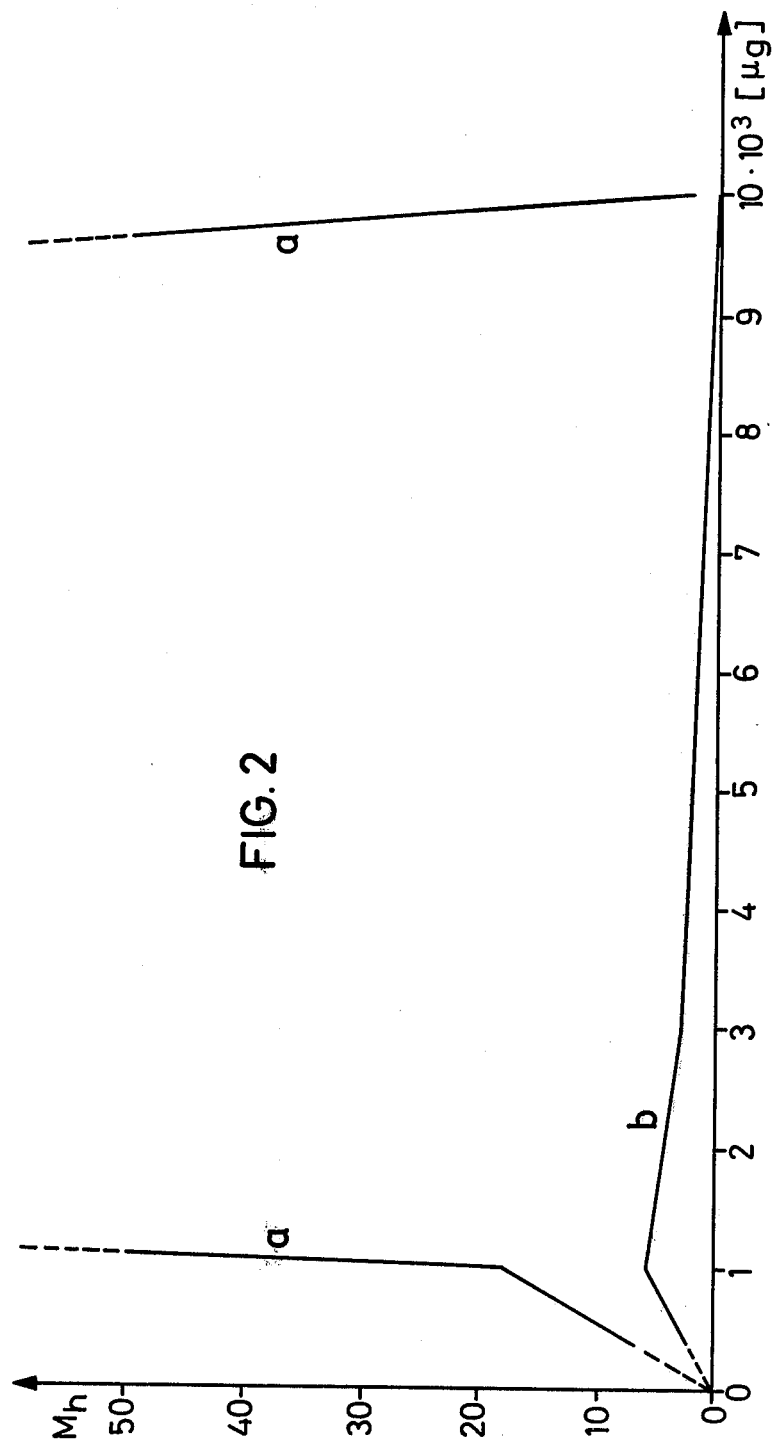
Figure 4:
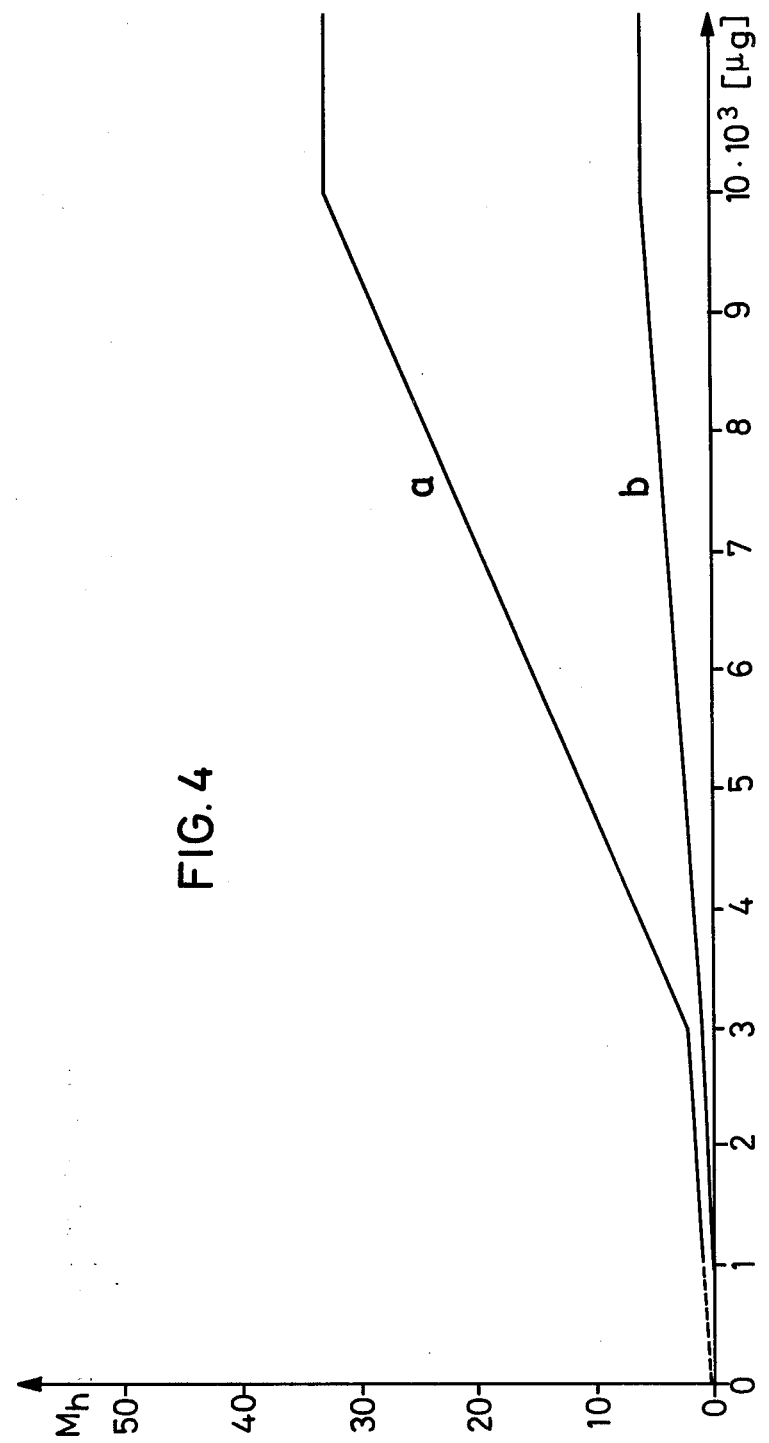
Figure 3:
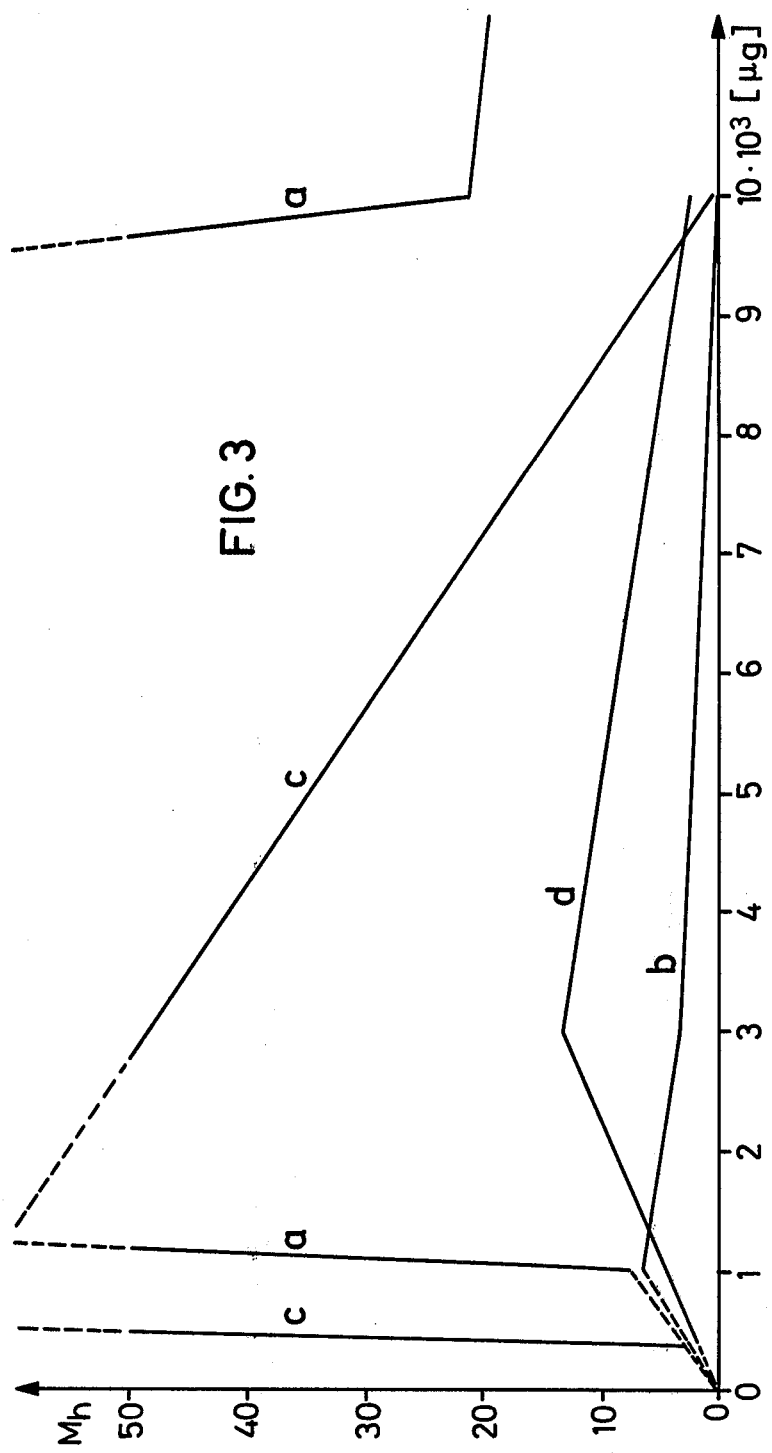

It is especially useful to determine this average if time is a characteristic factor to be observed. The advantage of this method is the fact that also "indefinite" longtime periods can be taken into account in for the result, i.e. dying and surviving specimen can be included in the results, because the reciprocal value of "indefinite" $1/\infty = 0$ (cf. L. Cavalli-Sforza: Grundbegriffe der Biometrie, G. Fischer Verlag, Stuttgart 1964). Accompanying FIGS. 1 to 4 show that the harmonic average depends on the dose of the poly(acrylic acid) salt.

FIG. (1)
  curve a: Poly(acrylic acid) with a molecular weight (MW) 51,500, at least 95% isotactic, unevenness of the molecular weights (UMW) 1.4;
  curve b: Poly(acrylic acid) with a molecular weight of 56,000, a maximum of 5% isotactic, UMW 1.2.

FIG. (2)
  curve a: Poly(acrylic acid) with a MW 24,600, at least 95% isotactic, UMW 1.3;
  curve b: Poly(acrylic acid) with a MW of 25,600, a maximum of 5% isotactic, UMW 1.4.

FIG. (3)
  curve a: Poly(acrylic acid) with a MW of 11,700, at least 95% isotactic, UMW 1.2;
  curve b: Poly(acrylic acid) with a MW of 14,000, a maximum of 5% isotactic, UMW 1.3;
  curve c: Poly(acrylic acid) with a MW of 15,900, a minimum of 95% isotactic, UMW 1.2;
  curve d: Poly(acrylic acid) with a MW of 15,700, a maximum of 5% isotactic, UMW 1.3.

FIG. (4)
  curve a: Poly(acrylic acid) with a MW of 7,500, a minimum of 95% isotactic, UMW 1.3;
  curve b: Poly(acrylic acid) with a MW of 8,600, a maximum of 5% isotactic, UMW 1.2.

What is claimed is:

1. An alkali metal salt of a polymer comprising at least 95 percent by weight of poly(acrylic acid), the balance if any being an ester of acrylic acid with an alcohol branched in the α-position, at least 75 percent by weight of said polymer being isotactic, said polymer having an average molecular weight from 5,000 to 40,000 as determined by dissolving said polymer in chloroform at a concentration, c, of 0.3 g/100 ml, 0.6 g/100 ml and 0.9 g/100 ml, measuring the viscosity of the solutions at 30° C., graphically determined the viscosity limit, [η], at which c=0, and calculating the molecular weight, M, from the equation $$[\eta] = 1.4(10^{-4}) \times \overline{M}^{-0.72},$$

and the ratio of the weight-average molecular weight to the numerical average molecular weight of said polymer, as determined by gel permeation chromatography, being from 1.1 to 2.

2. A solution or suspension comprising an antivirally effective amount of an alkali metal salt as claimed in claim 1 in a medicinally unobjectionable inert liquid.

3. A method of making an alkali metal salt as in claim 1 which comprises polymerizing an ester formed between acrylic acid and an alcohol branched in the α-position, at a temperature from −80° C. to 0° C. in the presence of 0.01 to 0.5 mole, per mole of ester, of an anionically-active catalyst and in an inert organic solvent free of oxygen and water and having a melting point below −80° C., for from 10 minutes to 24 hours, depending on the quantity of monomer used, whereby a poly(acrylic acid ester) having up to 25 percent by weight of atactic portions is obtained, removing said atactic portions to a great extent by agitation with isopropanol at a temperature from 15° C. to 30° C. for from 12 to 24 hours, further purifying the poly(acrylic acid ester) by precipitation fractionation if the ratio of the weight average molecular weight to the numerical average molecular weight exceeds 2, acidolytically saponifying the remaining essentially isotactic poly(acrylic acid ester), at a temperature from 80° C. to 120° C. for from 50 to 90 hours, with a mixture of water and a strong organic acid containing from 1 to 60 percent by volume of water and from 99 to 40 percent by volume of organic acid, the quantity of said mixture being from 5 to 20 times by weight that of the polymer, purifying the poly(acrylic acid) so obtained by dialysis against water, recovering the polymer by vacuum freeze drying, and then neutralizing said polymer to form said alkali metal salt.

4. The method as in claim 3 wherein said ester formed between acrylic acid and an alcohol branched in the α-position is isopropyl acrylate.

5. The method as in claim 3 wherein said polymer is purified by precipitation fractionation prior to acidolytic saponification.

* * * * *